United States Patent [19]
Walters et al.

[11] Patent Number: 5,942,425
[45] Date of Patent: *Aug. 24, 1999

[54] METHOD TO ACCESS NUCLEIC ACIDS FROM CELLS

[76] Inventors: Adriann H. Walters, 508 Cording Ave., Baltimore, Md. 21212; Daretta A. Bruchey, 5 Cormer Ct., Apt. 102, Timonium, Md. 21093

[ * ] Notice: This patent is subject to a terminal disclaimer.

[21] Appl. No.: 08/614,108

[22] Filed: Mar. 12, 1996

[51] Int. Cl.$^6$ .............................. C12N 13/00; G01N 1/18
[52] U.S. Cl. ..................... 435/173.7; 435/173.1; 435/173.4; 435/287.2; 435/287.6; 435/288.1; 435/306.1; 436/177; 436/523; 436/525; 436/527
[58] Field of Search .............................. 435/173.7, 173.4, 435/173.2, 173.1, 287.6, 306.1, 287.2, 288.1; 436/177, 523, 525, 527

[56] References Cited

U.S. PATENT DOCUMENTS

| | | | |
|---|---|---|---|
| 4,125,335 | 11/1978 | Blume | 366/209 |
| 4,202,634 | 5/1980 | Kraft | 366/111 |
| 4,295,613 | 10/1981 | Moore | 241/2 |
| 4,829,230 | 5/1989 | Perry | 323/273 |
| 4,874,137 | 10/1989 | Chiba | 241/301 |
| 5,374,522 | 12/1994 | Murphy | 435/6 |
| 5,376,527 | 12/1994 | Robson | 435/6 |
| 5,464,773 | 11/1995 | Melendez | 435/306.1 |

FOREIGN PATENT DOCUMENTS

| | | |
|---|---|---|
| 0 428 197 A2 | 5/1991 | European Pat. Off. . |
| 0 626 456 A1 | 11/1994 | European Pat. Off. . |
| WO 95/28409 | 10/1995 | WIPO . |

OTHER PUBLICATIONS

Hurley, Sarah S. et al., Rapid Lysis Technique for Mycobacterial Species, *J. Clin. Microbiol.* (1987) 25 2227–2229.
Reischl, Udo et al., PCR–Based Detection of Mycobacteria in Sputum Samples Using a Simple and Reliable DNA Extraction Protocol, *BioTechniques* (1994) 17 844–845.
Kox, L.F.F. et al., PCR Assay Based on DNA Coding for 16S rRNA for Detection and Identification of Mycobacteria in Clinical Samples, *J. Clin. Microbiol.* (1995) 33 3225–3233.
Shah, Jyotsna S. et al., Detection of *Mycobacterium tuberculosis* Directly from Spiked Human Sputum by Q–Beta Replicase–Amplified Assay, *J. Clin. Microbiol.* (1995) 33 322–328.

*Primary Examiner*—Laurie Scheiner
*Attorney, Agent, or Firm*—David W. Highet, Esq.

[57] ABSTRACT

The present invention relates to a sample processing method for rendering cellular components such as nucleic acids in a sample accessible. The method involves subjecting a sample of disrupted cells to sufficient agitation in the presence of particles to separate nucleic acids from other cellular components. A heat lysis process without other lysogenic agents or conditions is the preferred method of disrupting cells for the sample. Once accessed, the nucleic acids may be used in various molecular biology procedures.

14 Claims, No Drawings

METHOD TO ACCESS NUCLEIC ACIDS FROM CELLS

BACKGROUND OF THE INVENTION

Access to cellular components such as nucleic acids is imperative to a variety of molecular biology methodologies. Such methodologies include nucleic acid sequencing, direct detection of particular nucleic acid sequences by nucleic acid hybridization and nucleic acid sequence amplification techniques.

Although access to nucleic acids from the cells of some organisms does not involve particularly complex methodologies or harsh treatments, other organisms have cells from which it is particularly difficult to access nucleic acids or other cellular components. Organisms in the latter group include species of the genus Mycobacteria, yeast and fungi. Usually, the difficulty in cellular component access is a result of organism cell walls which are highly resistant to lysis or disruption, and/or the adherence of certain cellular components such as nucleic acids to cellular proteins and other cellular substances such as pieces of cell walls.

Due to the difficulties in attempting to access nucleic acids from mycobacterial organisms the methods utilized tend to be harsh and thus not very useful with non-mycobacterial organisms. Conversely, the methods used to disrupt cells and access nucleic acids from non-mycobacterial organisms are often not effective when used with mycobacterial organisms.

Two non-enzymatic methods which have been used to disrupt cells to access nucleic acids are the application of heat to cells (see U.S. Pat. No. 5,376,527) and physical agitation of cells in the presence of lysogenic chemicals with or without "minibeads". For example, DeWitt et al., *J. Clin. Micro.* 28 (11):2437–2441 (1990) describe the orbital shaking of samples containing mycobacterial cells in the presence of buffered phenol and sodium dodecyl sulfate (SDS), Hurley, S. S. et al., *J. Clin. Microbiol* 25 (11) 2227–2229 (1987) describe a combination of phenol extraction and physical rupture of mycobacterial cells with zirconium beads in a Biospec Products Mini-Beadbeater, and Shah, J. S. et al., *J. Clin Microbiol* 33 (2), 322–328 (1995) describe the lysis of heat-inactivated mycobacterial cells with the lysogenic agent guanidimium thiocyanate (GuSCN) and physical agitation with zirconium oxide beads. Also, U.S. Pat. No. 5,374,522 describes methods of disrupting cells by applying ultrasonic energy to the cells in the presence of beads, and Hurley et al., *Int. J. Systemic Bacteriology* 38 (2):143–146 (1988) describe physical agitation of samples containing mycobacterial cells in the presence of distilled phenol and zirconium beads.

As recognized in U.S. Pat. No. 5,374,522, rigorous physical grinding or shaking of organisms whether with or without beads presents considerable drawbacks. First, friction resulting from the physical interaction of grinding particles can create excessive heat which has deleterious effects on nucleic acids, and thus can render the nucleic acids unusable in subsequent hybridization procedures. Also, many of the organisms whose cells require such harsh conditions for extraction of cellular components are extremely pathogenic, and thus present health hazards when subjected to these physical manipulations in an open system. Also, the use of lysogenic chemical agents and/or enzymes such as SDS, GuSCN, proteinases, phenol/chloroform, etc. often adversely affects subsequent molecular biology processes for which the nucleic acids are accessed. For example, ionic and non-ionic detergents are known to inhibit nucleic acid amplification processes such as polymerase chain reaction (PCR) and strand displacement amplification (SDA), and carbon black which is commonly used to process glass beads is known to inhibit SDA.

SUMMARY OF THE INVENTION

The present invention provides a solution to the heretofore unaddressed problem of separating cellular components such as nucleic acids from other cellular components such as cellular proteins to which the nucleic acids are bound, even after cell lysis. This improvement in sample processing procedure is embodied in the present invention which is a method for rendering cellular components accessible by subjecting a sample of disrupted cells to agitation in the presence of particles to separate nucleic acids from other cellular components. Once accessed through use of the method of the present invention, cellular components such as nucleic acids may be used in various molecular biology procedures. The method of the present invention may also be combined with compatible cell disruption methodologies, such as heating, as a simultaneous or partially simultaneous step in a sample processing procedure.

DETAILED DESCRIPTION OF THE INVENTION

In a broad aspect, the method of the present invention provides a simple procedure for access to cellular components including nucleic acids in a form useful for subsequent molecular biology procedures. The method's simplicity results from the limited manipulation of a sample containing lysed cells. An additional element of safety is present when the method is combined with a cell disruption step including heating of the sample, because the heat necessary to disrupt cells is also sufficient to render any infectious organisms in the sample noninfectious.

When practiced with a heating step to disrupt cells, the method may entail sequential steps of heating the sample followed by physical agitation. Alternatively, the heating and physical agitation may occur as partially overlapping steps (partially simultaneously) or completely simultaneously.

After cells in a sample have been disrupted, the method of the present invention is performed to agitate the sample in the presence of particles such that cellular components such as nucleic acids are separated from other cellular components such as cellular proteins. A particular advantage of the method of the present invention is the lack of lysogenic agents with the particles during agitation of the sample. Methods such as those described described by DeWitt et al., supra, Hurley, S. S. et al. (1987) and (1988), supra and Shah, J. S. et al., supra require the use of the lysogenic agents SDS, phenol and GuSCN respectively. Lysogenic agents such as these often adversely affect subsequent molecular biology processes performed with the nucleic acids accessed. In contrast, the method of the present invention does not adversely affect subsequent molecular biology processes performed with the accessed nucleic acids.

Sufficient agitation of such samples of disrupted cells may be achieved with a variety of commercially available instruments. Exemplary instruments are the Biospec Mini-Beadbeater available from Biospec Products of Bartlesville, Okla., and the FastPrep™ instrument available from Savant Instruments of Holbrook, N.Y.

The sample agitation necessary for the method of the present invention wherein the goal is to separate cellular components from one another, is generally not as rigorous as the agitation which has been described as necessary to disrupt or lyse cells in a sample to release cellular components. For example, when used with phenol extraction to lyse *M. paratuberculosis, M. phlei, M. avium, M. fortuitum* and *M. scrofulaceum* cells, Hurley, S. S. et al. (1987), supra, describe mulling of the cells for three minutes in the prescence of zirconium beads using the Biospec Mini-Beadbeater. Similarly, Shah, J. S. et al., supra describe the lysis of heat-inactivated *M. tuberculosis* cells with the lysogenic agent, GuSCN, and the subjection of the cells to motion at 5,000 rpm for six minutes. In contrast, the agitation of the sample of disrupted cells in the method of the present invention is not as forceful as the mulling of cells described by Hurley, S. S. et al., nor does it continue for as long an amount of time as the agitation steps reported by Hurley, S. S. et al., or Shah, J. S. et al.

When agitation is applied to the sample in the method of the present invention with a Biospec Mini-Beadbeater, the instrument is set at "homogenize" for not more than about two minutes. Similarly, when used in the method of the present invention, the Savant Fast Prep instrument is set at a speed from about 4 to about 6.5 meters per second for not more than not more than about forty-five seconds. With the Savant instrument, a setting of 5 meters per second is preferred. In general, there is an inverse relationship of time and speed setting for effective agitation to achieve the goals of the present invention. These times of agitation permit optimal yield of accessible nucleic acids from disrupted cells samples. Although the samples may be subjected to longer times of agitation, the yield of accessible nucleic acids from such longer agitation times is not significantly greater than that from the agitation times reported above, because among other reasons, heat from friction in the sample became so great as to destroy some of the desired nucleic acid. Also, the cell lysis methods exemplified by Hurley, S. S. et al. (1987), supra and Shah, J. S. et al., supra which utilize more forceful agitation for longer times in a singular step of agitating a sample containing non-disrupted cells in the presence of particles and lysogenic agents have not been found sufficient alone to render desired cellular components accessible to the same extent as the method of the present invention wherein agitation with particles is applied to a sample containing cellular components from cells which are already disrupted.

The instrument which provides agitation should be capable of agitating at least one sample container in a manner which will result in particles in the sample moving through the sample to cause the separation of cellular components from one another, for example, the separation of nucleic acids from cellular proteins or cell wall fragments. The movement of particles through the sample is believed to cause the particles to move at least partially between the attached cellular components and thereby cause shearing of cellular component from cellular component.

As an example, the Savant FastPrep™ instrument agitates twelve sample containers in a manner which combines three types of motion:

(1) Axial reciprocation—sample containers are moved through a linear reciprocating motion in a direction defined by the axis of the container.

(2) Off-axis rotation—sample containers are rotated about an axis which is offset from the container axis by a small angle.

(3) Lateral reciprocation—sample containers are oscillated in a direction perpendicular to the containers' axis. The first two motions are synchronized such that one full axial reciprocation cycle corresponds to one full off-axis rotation. These synchronized rotations occur about sixty times per minute.

In contrast, the agitation of sample containers in a Biospec Mini-Beadbeater can be described as predominantly axial reciprocation, that is, a reciprocating motion parallel to the axis of the sample container. Also, a small component of lateral reciprocation is incidentally introduced due to compliance in the shock absorbing mounts and mechanical tolerances in the bearing and coupling components.

It is believed that the agitation of sample containers causes both cellular components of the sample as well as particles added to the sample to move within the sample container to cause the shearing of cellular components from one another.

The particles which are added to the sample may be of various compositions including, for example, glass, plastic, sand, silicates, latex, crystals, metals such as zirconium, metal oxides, etc. The particles may also be of various shapes, including for example, spheres, cubes, oval, capsule-shaped, tablet shaped, non-descript random shapes, etc., and may be of uniform shape or non-uniform shapes. Whatever the shape of a particle, its diameter at its widest point is generally in the range of from about 0.1 mm to about 0.15 mm. Particles with diameters greater than about 0.5 mm have been found to be not as effective in separating cellular components from one another in the method of the present invention.

One particularly advantageous means for adding particles to the sample is by use of a vehicle which retains a pre-determined amount of particles which when released into the sample and subjected to the method of the present invention renders nucleic acids in the sample accessible. A more complete description of suitable such vehicles is presented in co-pending U.S. patent application Ser. No. 08,614,230, filed on even date herewith, the disclosure of which is expressly incorporated herein by reference. The vehicles include a barrier to retain the particles, and one suitable embodiment is a capsule wherein the barrier is a frangible, disssolvable or meltable material which forms the surface of the capsule.

When the surface material is frangible, there may be included with the particles at least one "breaker particle" of greater density and/or size then the other particles. The impact of a breaker particle with the frangible material when the sample is agitated causes the material to break, and release the particles into the sample. Similarly, dissolvable or meltable surface materials will also cause the release of particles into the sample upon dissolution or melting, respectively. Once released into the sample, the particles are utilized in the method of the present invention.

The amount of particles added to a sample by any means is dependent upon the amount of and viscosity of the sample. Generally, a typical clinical sample from which a clinician would desire to access nucleic acids for diagnostic purposes has a volume of about 1 mL or less. However, other samples such as environmental samples or food product samples may have greater volumes, and other samples may have lesser volumes.

The viscosity of different samples can also vary, for example, within the category of clinical samples, a sputum sample is generally more viscous than a blood or urine sample. Similarly, the viscosities of different environmental samples will also vary.

As a general rule, in viscous samples such as sputum, the volume of particles added to a given volume of sample will be in a ratio of about 0.25:1 to about 1:1. It is believed that with less viscous samples, a lesser volume to volume ratio of particles to sample is sufficient to achieve the desired separation of cellular components from one another using the method of the present invention.

Oftentimes, agitation of a sample causes production of foam. This foam can interfere with liquid level sensing means if the sample is being subsequently processed with automated instrumentation. Thus, any suitable anti-foaming agent which would not interfere with the subsequent processing of the sample may be added thereto to address this potential problem. When the sample will be subjected to the SDA process, the addition of the anti-foaming agent FG/10 to the sample processing buffer in an amount of about 0.015% by volume has been found effective to substantially reduce foaming due to agitation. FG/10 is a food grade silicone emulsion which is commercially available from Dow Corning.

As is apparent, the sample which is subjected to agitation contains cellular components. Cellular components are all components from within the cells of an organism. Thus, prior to practice of the method of the present invention in a broad aspect, cells in or from a sample should be disrupted or lysed.

There are many sample processing techniques which have been used to disrupt or lyse cells. Examples of some known cell disruption methods are presented in the Background of the Invention section of this document. Other known cell disruption methods for mycobacterial cells and non-mycobacterial cells are presented below in Table I and Table II, respectively.

TABLE I

COMMERCIAL AND PUBLISHED METHODS
FOR LYSIS OF MYCOBACTERIA

| Author/Source | Method | Reference |
| --- | --- | --- |
| GenProbe | 15' sonication with lysing buffer and glass beads | Gen-Probe package insert |
| Pierre et al (1991) | 15' @ 95° C. with 0.1N NaOH, 2M NaCl, 0.5% SDS | J. Clin. Micro. 29 (4):712–717 |
| Hurley et al (1988) | 3' in minibead beater (Biospec Prod. Bartlesville, OK) with distilled phenol and 0.1-mm zirconium beads | Int. J. Systematic Bacteriology 38(2): 143–146 |
| Labidi | Mycobacteria converted to spheroblasts by growth in 1.4% glycine, 60 ug/ml D-cycloserine, 1 mg/mL lithium chloride, 200 ug/ml lysozyme, 2 mg/mL EDTA; then pelleted by centrifugation and heated 15' @ 65° C. in 1% SDS. | Archs. Inst. Pasteur. Tunis. 655(3–4):261–270 |
| Butcher et al (1988) | 3 hr @ 37° C. with 10 mg/ml subtilisin; then 3 hr @ 37° C. with 50 mg/mL lysozyme; then 12 hr @ 37° C. with 3 mg/mL pronase and 1% SDS. | Gut 29:1222–1228. |
| Wayne and Gross (1968) | 72 hr @ 37° C. with vigorous aeration; then 24 hr @ 37° C. anerobically with 10 uM EDTA, 1 mg/mL pronase; then 90' @ 56° C. with 5% DOC. | J.Bacteriol. 95(4): 1481–1482. |
| Brisson-Noel et al (1989) | Culture: 15' @ 95° C. with 0.1M NaOH, 2M NaCl, 0.5% SDS Blood: 4 hr @ 37° C. with 10 mg/mL lysozyme; then 16 hr @ 55° C. with 5 mg/mL pro K and 0.1% Triton X-100. | Lancet, 11/4:1069–1071. |
| De Wit et al | 30' @ 70° C. with 10 mM Tris-HCl, pH 8.5, 1 mM EDTA, 150 mM EDTA; then 3 hr @ 37° C. with buffered phenol: 1.5% SDS (1:1 volume) with orbital shaking. | J. Clin. Micro. 28(11):(1990) 2437–2441. |
| Roberts et al (1987) | 3 washes with 0.85% NaCl; then 15' @ 20° C. with 70% ethanol; then −70° C. | J. Clin. Micro 25(7): 1239–1243. |
| Picken et al (1988) | 16 hr @ 37° C. with 100 mg/ 0.8 mL lysozyme; then 1 hr ~37° C. with 1 mg/mL pro K; then 6 hr @ 50° C. with 2% SDS. | Mol. Cell. Probes 2:289–304 |
| Sjobring et al | SDS; then proteins removed by proteinase K; then precipitated with CTAB. | J. Clin. Micro 28(10): 2200–2204. |
| Whipple et al (1987) | 2 hr @ 37° C. with 8000 U/0.5 mL lipase; then 2 hr @ 37° C. with 5 mg/mL lysozyme; then 16 hr @ 50° C. with 2 mg/mL pro K and 1% SDS; then 10 min 0° C. with 0.4 volumes 5M potassium acetate. | J. Clin. Micro. 25(8): 1511–1515. |

TABLE I-continued

COMMERCIAL AND PUBLISHED METHODS
FOR LYSIS OF MYCOBACTERIA

| Author/Source | Method | Reference |
|---|---|---|
| Vary et al (1990) | 3 hr @ 37° C. with 10 mg/mL subtilisin; then 3 hr @ 50° C. with 5 mg/mL lysozyme; then 18 hr with 3 mg/mL pronase and 1% SDS; then 6 hr with fresh 3 mg/mL pronase. | J. Clin. Micro 28(5): 933–937 |
| Eisenach et al (1986) | 24–72 hr with D-cycloserine; 30' @ 37° C. with 1 mg/mL lysozyme in 15% sucrose, 50 mM Tris-HCl, 50 rnM EDTA; then 10' @ 25° C. with 0.1 mg/mL pro K; then 2 hr @ 37° C. with 1% SDS. | Am. Rev. Resp. Dis. 133 1065–1068 |
| Patel et al (1986) | 15' in light petroleum: chloroform:buffer (3:1:1) with vortexing and mixing; then centrifugation; then 2–4 hrs @ 37° C. with 10 mg/mL nagarase; then 2–4 hr @ 50° C. with 50 mg/mL lysozyme; then 12–36 hr @ 37° C. with 1% SDS and 3 mg/ml pronase added @ 12 hr intervals. | J. Gen Micro. 132:541–551 |
| Pao, et al | 30' @ 37° C. with 2 mg/mL lysozyme in 25% sucrose, 0.1M EDTA, 50 mM Tris-HCl; then 0.1% SDS in 0.1M Tris-HCl, 0.1M NaCl. | Tubercle 69:27–36. |
| Visuvanathan et al (1989) | 1 hr @ 70° C.; then 18 hr @ 37° C. with about 12.5 mg/mL subtilisin; then 5 hr @ 50° C. with about .31 mg/mL lysozyme; then 12 hr with about 2% SDS and 3 mg/mL pronase; then 8 hr with fresh 3 mg/mL pronase. | J. Micro. Methods 10:59–64. |
| Sritharin and Barker (1991) | NALC pellets suspended in 10 mM Tris-HCl, pH8.0, 1 mM EDTA and 1% Triton X-100 and boiled for 30 min. | Mol. Cell. Probes 5:385–395 |
| Kolk et al (1992) | NALC pellets subjected to digestion buffer of 5% Tween 20 and 10 mg/ml proteinase K and boiled for 15 min. | J. Clin. Micro. 30:2567–2575 |
| Victor et al. (1992) | NALC pellets centrifuged and vortexed | J. Clin. Micro. 30:1514–1517 |
| Shawar et al. (1993) | NALC pellets subjected to lysis buffer of 10 mM Tris HCl, 1 mM EDTA and 1% Triton X-100 and boiled for 30 min. | J. Clin. Micro. 31:61–65 |
| Plikaytis et al. (1991) | NALC pellets suspended in buffer containing 20 mg/ml lysozyme; 0.5M NaOH and 1% SDS added and boiled for 5 min. | Am. Rev. Respir. Dis. 144:1160–1163 |
| Cousins et al. (1992) | NALC pellets heated at 75° C. for 45 min. and lysed with 2 mg/ml lysozyme, 1% SDS and 100 ug/ml proteinase K | J. Clin. Micro. 30:255–258 |
| Del Portillo et al. (1991) | sputum diluted in $H_2O$ and boiled for 10 min., then incubated at 37° C. in 2 mg/mL lysozyme, and 1% SDS and 250 ug/uL proteinase K added before incubating at 65° C. for 20 min. | J. Clin. Micro. 29:2163–2168 |
| Buck et al. (1992) | NALC pellets of clinical samples centrifuged at 16,000 x g for 10 min., then sonicated for 30 min., and boiled for 10 min. | J. Clin. Micro. 30:1331–1334 |
| Savic et al. (1992) | samples liquified and pelleted by sputolysin procedure; pellets boiled for 10 min., mixed with glass beads, incubated with 40 ug proteinase K and 0.5% Tween 20 at 37° C. for 30 min and sonicated at 60° C. for 20 min. | J. Inf. Dis. 166:1177–1180 |

TABLE I-continued

COMMERCIAL AND PUBLISHED METHODS FOR LYSIS OF MYCOBACTERIA

| Author/Source | Method | Reference |
|---|---|---|
| Shankar et al. | sample centrifuged and pellet subjected to 0.1N NaOH, 1M NaCl and 0.5% SDS, then heated at 95° C. for 15 min. | Lancet 33:5–7 |
| Pierre et al. (1991) | samples liquified and pelleted by SDS procedure, then pellets incubated with 0.1N NaOH, 2M NaCl and 0.5% SDS at 95° C. for 15 min. | J. Clin. Micro. 29:712–717 |
| Thierry et al. (1992) | same as Pierre et al 1991 above | Mol. Cell. Probes 6:181–191 |
| Brisson-Noel et al. (1989) | same as Pierre et al. 1989 above | Lancet, Nov. 4 1069–1071 |
| DeWit et al. (1990) | pleural fluid mixed with polyethylene glycol (PEG), centrifuged and pellet extracted for 3 hours at 37° C. with 10% SDS, buffered phenol. | J. Clin. Micro. 28:2437–2441 |
| Sjoborg et al. (1990) | samples liquified and pelleted by sputolysin procedure; pellet suspended in 50 mM Tris, boiled for 5 min. and sonicated with glass beads at 50° C. for 15 min. | J. Clin. Micro. 28:2200–2204 |

Legend:
SDS, sodium dodecyl sulfate; CTAB, cetyl trimethyl ammonium bromide; pro K, proteinase K; Tris-HCl, Tris(hydroxymethyl) aminomethane hydrochloride; EDTA, ethylene diamine tetraacetic acid.

TABLE II

Examples of Published Lysis Protocols for Non-mycobacterial Cells

| Author/Sample | Method | Reference |
|---|---|---|
| deKloet/yeast | 1' @ 32° C. with 20 U/ml lyticase | J. Micro Meth. 2:189–196 |
| Monsen et al/ streptococci (1983) | 5–60' @ 37° C. with 0.1 mg/ml mutanolysin in 5 mM EDTA, 0.5% Triton X-100 | FEMS Micro. letters 16:19–24. |
| Chassy/gram+ Gluffrida bacteria (1980) | 60' @ 37° C. with 1.2 mg lysozyme per 1.0 mg bacterial cells | Appl. Env. Microbiol. 39(1):153–158. |
| Gross-/mammalian Bellard et al | 12 hr @ 37° C. with 50 mg/ml pro K. | Eur. J: Biochem. 36:32–38 |
| Grimberg/blood et al cell (1989) nucleii | 2 hr @ 37° C. with 1 mg/ml pro K in 10 mM Tris-HCL, 10 mM NaCl, 10 mM EDTA | Nucleic Acids Res. 17(20):8390 |
| Moreno/blood et al (1989) | 1 hr @ 50° C. with 200 ug pro K in 0.4M Tris-HCl, 0.1M EDTA, 1% SDS | Nucleic Acids Res. 17(20):8393 |
| Birnboim &/E. coli Doly (1979) | 30' @ 0° C. with 2 mg/ml lysozyme; then 5' @ 0° C. with 0.2N NaOH, 1% SDS | Nucleic Acids Res. 7(6):1513–1523 |
| Klein/E. coli et al (1980) | 15' @ 20° C. with 1 mg/ml lysozyme in 10 mM Tris-HCl. | Plasmid 3:88–91 |

Heating of a sample containing cells has been found to be one of the preferred methods of disrupting cells, because it serves a dual purpose of disrupting the cells to release cellular components and rendering any infectious organisms in the sample noninfectious. For example, as taught in U.S. Pat. No. 5,376,527 and U.S. Ser. No. 08/287,734, filed Aug. 9, 1994, both disclosures of which are espressly incorporated herein by reference, application of a lysis effective amount of heat alone, in the absence of other lysogenic agents or other lysogenic conditions, will lyse even the difficult-to-lyse cells of mycobacterial organisms. This lysis effective amount of heat is also sufficient to render infectious organisms such as *Mycobacterium tuberculosis* organisms noninfectious, and thus safe for handling. The combination of heating a sample to disrupt cells and agitation of the sample with particles to separate cellular components from one another yields readily accessible nucleic acids separated from cellular proteins in a noninfectious environment.

This result is not believed to be achievable with either heat alone or agitation with particles alone. Prior to the present invention heat was used to lyse cells and agitation with beads was used to lyse cells. However, it is not believed that, prior to the present invention, agitation with particles was applied to samples of cellular components from already lysed cells to provide access to nucleic acids.

Heating of a sample may be accomplished by any suitable method. The heat range for disrupting the cells of a particular organism is readily obtainable by titrating different temperatures for different amounts of time against release of desired cellular components from the cells of an organism. The heating will lyse the cells of the organism with subsequent release of intracellular components. One limitation on the heating is that the particular intracellular component of interest not be susceptible to destruction by the heat. Suitable heating means include water baths, microwave ovens, convection ovens, forced hot air ovens, and the like.

The heating time required for exposing intracellular components in the sample generally ranges from about two minutes to about thirty minutes. The amount of heat and time of heat is readily found by sampling a portion of the cells of the organism to be lysed and examining for signs of lysis (e.g., detection of intracellular components), depending on the source from which the intracellular component is to be obtained.

The cells of the organism to be lysed can be in $H_2O$, but also can be in suitable buffers such as Tris-buffered saline (50 mM Tris-HCl, 150 mM NaCl, pH 8.0), phosphate-buffered saline (50 mM sodium phosphate, 150 mM NaCl, pH 8.0), polymerase chain reaction buffer (10 mM Tris-HCl, pH 8.8, 50 mM KCl, 1.5 mM $MgCl_2$), REACT6 (buffer name REACT6 is registered by Bethesda Research Labs) (50 mM Tris-HCl, pH 7.1, 50 mM NaCl, 50 mM KCl, 6 mM $MgCl_2$), sodium phosphate (pH 5.0 to 12.0), Trizma 9.0 (sigma:Trishydroxyaminomethylamine), and detergents such as 0.5% Tween 20 and 0.5% Nonidet P-40. Optionally, the heated sample can be centrifuged, making available the supernatant and pellet for subsequent use.

A typical protocol for lysing mycobacterial cells with heat comprises centrifugation of a sample believed to contain mycobacterial cells for a brief amount of time (e.g., about five minutes) and discarding the resultant supernatant. The pellet may then be reconstituted in any suitable buffer. Then, the sample is subjected to a brief incubation period with a lysis effective amount of heat.

As stated above, the lysis effective amount of heat can be provided from a variety of sources including water baths, microwave ovens, convection ovens and forced hot air ovens. However, there are a number of advantages associated with the use of forced hot air ovens including the maintenance of a clean and dry external environment for sample tubes, more efficient and rapid heat transfer than convection ovens and heating blocks, and excellent reproducibility. These advantages are taught in more detail in U.S. Pat. No. 5,376,527, the disclosure of which is expressly incorporated herein by reference.

Forced hot air heating can be achieved with any commercially available forced hot air oven which can achieve a temperature range from ambient to about 150° C. and can preferably go from ambient temperature to a desired temperature of about 100° C. to 105° C. in about two minutes. The velocity of the air moving through the oven is about 3 meters/second to about 6 meters/second. The pattern of the air flow within the oven should be such that all sample tubes are efficiently heated to desired temperature consistently and uniformly. In commercially available forced hot air ovens, the air flow is generally parallel or perpendicular to the tube or container holding the sample, however any air flow pattern or configuration which results is substantially complete immersion of the tube or container in the hot air is acceptable.

In addition, due to the consistency of the heat transfer with forced hot air heating, it has been found that a more consistent loss of viability or killing of mycobacterial organisms occurs. The killing of the mycobacterial organism can be as important as its lysis because of the infectious nature of these organisms. Inconsistency in the killing of mycobacterial organisms presents an unsafe environment for those researchers attempting to lyse mycobacteria to obtain nucleic acid.

In all of the above-described heating methods, the sample is held in a closed tube or other container during heating. Thus, the vapor pressure in the tube or container increases with increasing heat in accordance with the relationship between pressure, absolute temperature and volume as set forth in Charles Law. A simple manner in which to determine the pressure inside the tube or container is by reference to readily available tables such as those presented in the Handbook of Chemistry and Physics published by the Chemical Rubber Company ("CRC").

The following examples illustrate specific embodiments of the invention described in this document. As would be apparent to skilled artisans, various changes and modifications are possible and are contemplated within the scope of the invention described.

EXAMPLE 1

Access to Nucleic Acids by Lysis of Mycobacterial Cells with Phenol/Chloroform Extraction This experiment was performed to demonstrate the state of the present art for extraction of nucleic acids from mycobacterial cells as a comparative example for other Examples which demonstrate the method of the present invention.

Materials

The following materials were used:

Mycobacterium tubercluosis strain H37Rv (ATCC #27294)

M/15 Phosphate Buffer, pH 6.8 (Remel Catalog #21-249)

KPDG Buffer (32.48 mM $KPO_4$, 7.5% DMSO, 3% Glycerol, pH 8.0)

Phenol/Chloroform Reagents

Tris-EDTA-NaCl Buffer (TEN Buffer, 50 mM Tris, 100 mM EDTA, 150 mM NaCl, pH 8.0)

Subtilisin (12.5 mg/mL)

Lysozyme (100 mg/mL)

20% SDS (Sigma L-4390, Lot 93H0425)

Pronase E (60 mg/mL)

Phenol/Chloroform/Isoamyl Alcohol (Sigma P3803, Lot 14H0279)

Chloroform/Isoamyl Alcohol (Sigma C-0549, Lot 44H0191)

7.5 M $NH_4$-acetate (Sigma A-1542, Lot 33H0287)

100% and 70% Ethanol (IBI Lot 5B19-50)

RO/DI Water (Lot 94-31 A)

SDA and Detection Reagents

KPDG Buffer (32.48 mM $KPO_4$, 7.5% DMSO, 3% Glycerol, pH 8.0)

Pre-Amp Buffer ($KPO_4$, DMSO, Glycerol)

Decontamination Drydown Mix consisting of 41.25 mM $KPO_4$, 5% Trehalose, 0.05 mg/mL acetylated BSA, 1 mM Mg Acetate, 1.1 mM dNTP, 2.75 mM dUTP, 2.75 uM Primers, 0.1375 uM Bumpers, 0.275 uM Adapter, 1 unit UDG Amplification Drydown Mix consisting of 41.25 mM $KPO_4$, 5% Trehalose, 0.05 mg/mL acetylated BSA, 1 mM DTT, 1000 copies/uL Signature, 17.875 mM Mg Acetate, 250 units Hinc II, 4 units exo-klenow, 2 units UDI Dummy Decontamination, Amplification Devices (DADs) (Lots 95-20, 22, 16)

Assay Devices (AD) (Lot 95-01)

Mtb Hybridization Buffer (Lot 95-50A)

Genus Hybridization Buffer (Lot 95-32D)

Signature Hybridization Buffer (Lot 95-119A)

Systems Fluid (Lot 95-01A)

Stringency Wash (Lot 95-01A)

LumiPhos™ 530 (Lot L5 40202) (available from Lumigen of Southfield, Mich.)

Preparation of Phenol/Chloroform (P/C) Extracted, Diluted Samples

M. tuberculosis H37Rv cells from a log phase culture were washed with M/15 Phosphate buffer to remove any extracellular DNA. Cells were resuspended in the phosphate buffer, enumerated and diluted (in phosphate buffer) to working concentrations. Dilutions were aliquotted into 0.25 mL volumes to give concentrations of $10^2$, $10^3$ or $10^4$ particles per 0.25 mL sample.

One mL of KPDG was added to each sample. Samples were centrifuged 5 minutes at 12,000×g to pellet the *M tuberculosis* cells. After decanting the supernatant, this step was repeated. The resulting pellet was resuspended in a final 1 mL of TEN Buffer, making the sample milieu compatible with subsequent enzymatic reactions.

The samples were then subjected to standard phenol/chloroform extraction as follows. A 1 mL aliquot of sample was centrifuged for 10 minutes at 12,000×g and the supernatant decanted. To the pellet was added, 0.25 mL of subtilisin at 12.5 mg/mL. Then the sample was incubated for 3 hours at 37° C., and 50 ul of lysozyme was added at 100 mg/mL and the sample incubated for 3 hours at 55° C. Then, 25 ul of 20% SDA and 25 ul of pronase E was added at 60 mg/mL and the sample incubated overnight at 37° C. Finally, another 25 ul of pronase E was added and the sample incubated for 3 hours at 55° C.

Following these enzymatic reactions, the samples were subjected to two consecutive phenol/chloroform/isoamyl alcohol extractions and then one chloroform/isoamyl alcohol extraction. The DNA from the samples was then precipitated using ammonium acetate and 100% ethanol and centrifuged at 12,000×g for 15 minutes. The DNA pellets were washed once with 70% ethanol, centrifuged again, air dried and finally disolved in water.

These P/C extracted samples in 30 $\mu$l of water were diluted 1:2 in 2×KPDG buffer (potassium phosphate, DMSO, glycerol) in order to get the entire sample into the equivalent of 1×KPDG resulting in each sample being 60 $\mu$l of P/C extracted sample in 1×KPDG.

Amplification and Detection of Nucleic Acid from P/C Extracted Samples

A 30 $\mu$l aliquot of each sample ("undiluted sample") was then run directly in an SDA assay with the following reagents under the following conditions:

The 30 ul sample was combined with 5 ul of Pre-Amp Buffer in a 0.5 mL microcentrifuge tube. This sample was heated for 3 minutes in a boiling water bath. To this was added 10 ul of the Decontamination Drydown Mix and an amplicon decontamination reaction was conducted for 50 minutes at 41° C. Amplicon decontamination was conducted using a method well known to those skilled in the art from references such as U.S. Pat. No. 5,035,996, the disclosure of which is expressly incorporated herein by reference. Briefly, during a nucleic acid amplification process, the nucleotide dUTP is substituted for dTTP, and thus all products which are replicated from the target DNA sequence (amplicons) contain dUTP instead of dTTP. Then, prior to a nucleic acid amplification process, the sample is contacted with the enzyme uracil DNA glycosylase (UDG). The UDG cleaves the glycosidic bond between uracil and the sugar deoxyribose when dUTP is incorporated into a DNA molecule. Thus, amplicons from previous nucleic acid amplification processes are rendered non-amplifiable (i.e. are not suitable as templates for replication). Therefore, only true target sequence in the sample will serve as template for nucleic acid amplification.

Following amplicon decontamination, 10 ul of the Amplification Drydown Mix was added and the sample incubated for another 2 hours at 41° C. to permit Strand Displacement Amplification (SDA) process to proceed. SDA is a nucleic acid amplification process well known to those skilled in the art. Briefly, Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occur concurrently in the reaction mix. This is in contrast to the PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an $\alpha$-thio deoxynucleoside triphosphate ($\alpha$thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an $\alpha$-thio dNTP is incorporated are HincII, HinduII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. 1992. *Proc. Natl. Acad. Sci USA* 89, 392–396, Walker, et al. 1992. *Nucl. Acids Res.* 20, 1691–1696 and in U.S. Pat. No. 5,270,184 (hereby expressly incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATP$\alpha$S"). The extension products of $S_1$ and $S_2$ are thereby displaced from the original target sequence template by extension of $B_1$ and $B_2$. The displaced, single stranded extension products of the amplification primers serve as a targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

The SDA reaction originally reported in the publications cited above ("conventional SDA") is typically conducted at a temperature between about 35° C. and 45° C., and is capable of $10^8$-fold amplification of a target sequence in about 2 hours. Recently, SDA has been adapted for higher reaction temperatures (about 45–65° C.—"thermophilic SDA" or "tSDA"). tSDA is capable of producing $10^9$–$10^{10}$ fold amplification in about 15–30 min. at about 50–60° C. In addition to increased reaction speed, there is a significant reduction in non-specific background amplification in tSDA as compared to conventional SDA.

Detection of amplified target Mycobacterium genus sequence and M tuberculosis complex species sequence ($IS_{6110}$) was conducted in an assay only format on the BDProbeTec™ instrument. This detection system is fully described by C. A. Spargo et al. in Molec. Cellular Probes 7:395–404 (1993).

The BDProbeTec™ instrument is an automated system for performing SDA assays. The particular details of embodiments of the BDProbeTec™ instrument which was used to automatically perform the detection of amplified target sequences after SDA assays in this Example are disclosed in U.S. patent application Ser. No. 08/409,821, filed Mar. 24, 1995, the disclosure of which is expressly incorporated herein by reference.

To the other 30 μl aliquot of each sample was added 970 μl of KPDG to bring the volume up to 1 ml. A 30 μl aliquot of each of these samples ("diluted sample") was then subjected to the same SDA process described above in order to mimic a 1:33 dilution seen with standard wash/lysis procedures.

Results

Presented below in Table 1 are the results of the SDA and detection assays for M. tb. species ($IS_{6110}$) and M. Genus.

samples, P/C extraction allows optimal yields of nucleic acid at 10,000 cells per reaction.

EXAMPLE 2

Access to Nucleic Acids by Lysis of Mycobacterial Cells with Heat

The materials used in this Example were the same as those used in Example 1, except that the phenol/chloroform extraction reagents were not used.

Preparation of Heat Lysed Samples

Samples of the M. tuberculosis H37Rv cells were prepared in the same manner as those of Example 1 except final resuspension was in 1 mL of KPDG, not TEN Buffer. The samples were then heated for 30 minutes at 105° C. in a forced hot air oven.

Amplification and Detection of Nucleic Acid from Heat Lysed Samples

The samples were subjected to SDA and chemiluminescent detection assays in the same manner as were the samples of Example 1.

Results

Presented below in Table 2 are the results of the SDA and detection assays of this Example.

TABLE 2

| No. Mtb cells | IS6110 RLU | No. Positive | Genus RLU | No. Positive |
|---|---|---|---|---|
| $10^2$ | 35 | 7/10 | 3 | 2/10 |
| $10^3$ | 135 | 10/10 | 4 | 5/10 |
| $10^4$ | 875 | 7/7 | 197 | 7/7 |

As can be seen from the results presented in Table 2, heat alone for DNA access showed comparable results against the P/C extraction of Example 1 for M. tb. complex sequence (IS6110). However, for Genus sequence, there was a measurable decrease in % positivity and RLU signal.

EXAMPLE 3

Access to Nucleic Acids by Agitation of Samples

Because agitation of samples of M. tb. cells with particles by itself does not render the M. tb. organisms non-infectious, this comparative example was not actually performed due to safety concerns. However, data from Hurley, S. S. et al. (1987) supra provides the following data regarding yield of useable nucleic acids from agitation of mycobacterial cell samples.

Hurley, S. S. et al. compared the yield of DNA and RNA from mycobacterial cells mulled and ruptured in a Biospec

TABLE 1

| | UNDILUTED P/C SAMPLES | | | | DILUTED P/C SAMPLES | | | |
|---|---|---|---|---|---|---|---|---|
| No. Mtb Cells | IS6110 RLU | No. Positive | Genus RLU | No. Positive | IS6110 RLU | No. Positive | Genus RLU | No. Positive |
| $10^2$ | 20 | 7/10 | 33 | 6/10 | 3 | 2/10 | 5 | 2/10 |
| $10^3$ | 334 | 10/10 | 70 | 9/10 | 19 | 4/10 | 31 | 6/10 |
| $10^4$ | 1014 | 10/10 | 433 | 10/10 | 216 | 10/10 | 60 | 10/10 |

RLU - Relative Light Units

As can be seen from the results in Table 1, P/C extraction allows near optimal yields of nucleic acid between 100 and 1000 cells per reaction in undiluted samples. With diluted Mini-Beadbeater with 0.1 mm zirconium beads and phenol to DNA and RNA recovered from mycobacterial cells lysed in a Ribi pressure cell. The results of this comparison showed that when equal numbers of cells were used in both the Ribi pressure cell and the Mini-Beadbeater, the Mini-Beadbeater preparations yielded three to four times more DNA. However, the range of fragment sizes from the Mini-Beadbeater preparations were greater. Also, the best data presented by Hurley, S. S. et al. shows nucleic acid extracted from mycobacterial samples containing $10^5$ cells/ml using agitation with zirconium beads and phenol. In contrast, as shown in Example 4 below, the present invention wherein already disrupted cells are subjected to agitation provides sufficient nucleic acid for SDA from samples containing as little as 400 mycobacterial cells/ml of sample (i.e. $10^2$ mycobacterial cells/0.25 ml of sample).

EXAMPLE 4

Access to Nucleic Acids by Agitation of Heat Lysed Samples

The materials used in this Example were the same materials as were used in Example 2 with the addition of 0.1 mm glass beads (Cole-Parmer Catalog #11079-101). The samples were then prepared, and subjected to the same heat lysis process as were the samples of Example 2.

One mL of glass beads which had been washed three times with equal volume of KPDG buffer in an attempt to remove any possible inhibitors of SDA was added to the samples. The samples were then loaded into a Biospec 101 Mini-Beadbeater instrument which was run on a setting of homogenize for 1.5 minutes. (The Biospec 101 Mini-Beadbeater has four speed settings from slowest to fastest: slow, mix, fast and homogenize.)

The samples were subjected to SDA in the same manner as were the samples of Example 1.
Results Agitation of the samples with beads after heating produced 100% positivity for the *M. tuberculosis* SDA target at $10^2$ particles, and 100% positivity for the Mycobacterium genus target at $10^4$ particles. This method generated SDA signals that were 1.5 to 27 times greater than heat alone (Example 2), and 1.5 to 6 times that of phenol/chloroform extraction (Example 1). Increases were dependent on SDA target and particle input level. Heat plus agitation with beads produced more robust and consistent signals than the other two methods, resulting in better low end sensitivity.

EXAMPLE 5

Access to Nucleic Acids by Agitation of Heat Lysed Simulated Clinical Specimens The materials used in this Example were the same as those used in Example 4. The *M. tuberculosis* cells were prepared to their dilution in phosphate buffer in the same manner as were the samples of Example 1. However, the sample dilutions in phosphate buffer were then used to spike 0.25 mL volumes of a negative NALC sediment pool to give concentrations of 100, 200, 500 or 1000 particles per 0.25 mL of sediment. These samples were designed to minic a clinical specimen.

One mL of KPDG was added to each sample. Samples were then centrifuged for 5 minutes at 12,000×g to pellet the *M. tuberculosis* cells. After decanting the supernatant, this wash step was repeated. The resulting pellet was resuspended in a final lmL of KPDG, making the sample milieu compatible with SDA. One set of samples (n=10 per particle level) was heated 30 minutes at 105° C. in a forced hot air oven. One mL of the washed glass beads were added to each sample. Samples were then subjected to agitation in a Bio 101 Mini-Beadbeater instrument at homogenize speed for 1.5 minutes. A second set of samples was subjected to the heat treatment only. Samples were then subjected to SDA in the same manner, as were the samples of Example 1.
Results Heat treatment followed by agitation with beads produced 100% positivity for the *M. tuberculosis* SDA target at 100 particles per NALC sediment, and 100% positivity for the Mycobacterium genus SDA target at 1000 particles per NALC sediment (80% genus positivity was seen at 200 and 500 particles). Heat treatment alone did not produce 100% positivity at any particle level for either target. Heating plus agitation with beads increased mean SDA signals 2 to 17 times that of heating alone (increases dependent on target and particle input level). Heating followed by agitation with beads made more DNA available for amplification than heat alone, resulting in better low end sensitivity.

EXAMPLE 6

Optimization of Particles Used in Agitation to Access Nucleic Acids

The materials used in this Example were the same as those used in Example 5, with the addition of 0.1 mm zirconia/silica beads (Cole-Parmer Catalog #11079-101Z).

The samples were prepared in the same manner as those in Example 5, with the concentration being 500 particles of *M. tuberculosis* per 0.25 mL of NALC sediment pool.

All samples were heated for 30 minutes at 105° C. in a forced hot air oven. Following heat treatment, one set of samples received 1 mL of washed glass beads, one set received 1 mL of washed zirconia/silica beads, and one set was left as is as a heat only control. Samples containing beads were agitated as in Example 5. Samples were subjected to SDA under the same conditions as the samples in Example 1.
Results:

Use of zirconia/silica beads resulted in 100% positivity for the *M. tuberculosis* and Mycobacteria genus SDA targets. Using glass beads dropped the positivity to 70% for the genus target, and heat only dropped the positivity of both targets (50% and 13% respectively). In addition, there was signal attenuation seen with the internal SDA control in the glass bead samples, indicating that the glass beads were inhibiting amplification (even after washing). The zirconialsilica beads demonstrated no such inhibition. The use of zirconia/silica beads to access nucleic acids results in more favorable amplification conditions than the glass beads due to the presence of the SDA inhibitor carbon in the glass beads.

While the invention has been described with some specificity, modifications apparent to those of ordinary skill in the art may be made without departing from the scope of the invention. Various features of the invention are set forth in the following claims.

That which is claimed is:

1. A method for rendering nucleic acids, in a sample containing already disrupted cells, accessible comprising the steps of:
   (a) further disrupting the cells to release nucleic acids and cellular components other than nucleic acids into the sample; and
   (b) subjecting the nucleic acids and cellular components other than nucleic acids to agitation with particles, said agitation being sufficient to separate the nucleic acids from the cellular components other than nucleic acids.

2. The method of claim 1 wherein the cellular components are from mycobacterial cells.

3. The method of claim 1 wherein the particles, at their widest point, have diameters not greater than 0.5 mm.

4. The method of claim 1 wherein said particle diameters are between about 0.1 mm and about 0.15 mm.

5. The method of claim 1 wherein the particles are spherical.

6. The method of claim 1 wherein the particles are composed of zirconium and silica.

7. The method of claim 1 wherein the volume to volume ratio of particles to sample is between about 0.25:1 and about 1:1.

8. The method of claim 1 wherein cells in the sample are disrupted simultaneously with the subjection of the sample to said agitation.

9. The method of claim 1 wherein cells in the sample are disrupted by subjecting the sample to heat at a temperature and for a time sufficient to render infectious organisms in the sample noninfectious.

10. The method of claim 9 wherein the temperature for heating is from about 95° C. to about 105° C. and the time of heating is from about two minutes to about thirty minutes.

11. The method of claim 9 wherein the said heat is provided as forced hot air.

12. The method of claim 8 wherein cells in the sample are disrupted by subjecting the sample to heat at a temperature and for a time sufficient to render infectious organisms in the sample noninfectious.

13. The method of claim 12 wherein the temperature for heating is from about 95° C. to about 105° C. and the time of heating is from about two minutes to about thirty minutes.

14. The method of claim 12 wherein the said heat is provided as forced hot air.

* * * * *